United States Patent [19]

Constant et al.

[11] Patent Number: 4,884,437
[45] Date of Patent: Dec. 5, 1989

[54] METHOD AND APPARATUS FOR MEASURING FLUID-FLUID INTERFACIAL RHEOLOGICAL PROPERTIES

[75] Inventors: W. David Constant; Joanne M. Wolcott, both of Baton Rouge; Vivian J. Cambridge, Slidell, all of La.

[73] Assignee: Louisiana State University, Baton Rouge, La.

[21] Appl. No.: 229,702

[22] Filed: Aug. 8, 1988

[51] Int. Cl.$^4$ ............................................. G01N 11/00
[52] U.S. Cl. ....................................................... 73/54
[58] Field of Search ....................... 73/54, 64.4, 863.11

[56] References Cited

U.S. PATENT DOCUMENTS 4,425,810  1/1984  Simon et al. ..................... 73/863.11

FOREIGN PATENT DOCUMENTS 122933  9/1981  Japan ........................................ 73/54
150328 11/1981  Japan ........................................ 73/54

Primary Examiner—Stewart J. Levy
Assistant Examiner—Joseph W. Roskos

[57] ABSTRACT

This invention is a new, novel method and apparatus for the measurement of fluid-fluid interfacial shear viscosities. The method and apparatus are simple in design and conducive to routine measurements. The viscosities are measured by observation of the unsteady state deformation of the interface after a slowly rotating cylindrical cell containing the sample is abruptly halted. The deformation is established with tracer particles located at the interface between the two fluids in the sample. Correlations show the relationship of the traversed angle of the particles to the interfacial shear viscosity, the viscosities and densities of the bulk phases, and the sample dimensions. The method is sufficiently sensitive to allow measurements of interfacial shear viscosities ranging from 0.001 to 5.0 surface poise depending on cell geometry and liquid viscosity.

20 Claims, 2 Drawing Sheets

METHOD AND APPARATUS FOR MEASURING FLUID-FLUID INTERFACIAL RHEOLOGICAL PROPERTIES

BACKGROUND OF THE DISCLOSURE

The concept that the interface between two fluids may exhibit rheological properties different from those of the bulk phases has been known for some time. Since this early observation, the rheological properties of interfacial films have been the subject of extensive theoretical and experimental investigations. Experimental studies suggest that the rate of coalescence of bubbles in foams and emulsions, and therefore the stability of foams and emulsions, is dependent on the rheological properties of the fluid-fluid interface. Interfacial viscosities are believed to contribute to the suppression of interfacial turbulence by surfactants. They are also considered to play an important role in mass transfer across fluid-fluid interfaces and in solvent extraction processes. In addition, interfacial rheological phenomena have been found to affect oil displacement in a variety of oil recovery processes including water flooding, micellar/polymer flooding, alkaline flooding, and steam or $CO_2$ processes employing foam for mobility control.

In order to quantitatively assess the role of interfacial viscosity in fluid-fluid interactions, one must be able to accurately measure this property. Much effort has been devoted to devising procedures for the measurement of interfacial rheological properties. Only the more recently developed procedures have proven reliable as previous methods were plagued with difficulties. Four currently accepted procedures for measuring surface shear properties at gas-liquid interfaces are the disk, the knife-edge, the thin biconical bob, and the deep channel interfacial viscometers. For the first time, recently, agreement between viscosity measurements was obtained supporting the validity of these procedures.

The disk, knife-edge and thin biconical bob instruments share similar designs. In all three cases, one measures the torque required to hold the bob stationary as the disk containing the fluids rotates with a constant angular velocity. Small deflections of the torsion wire from rest (where the angular velocity of the dish is zero) are determined by reflecting a low power laser beam off a small mirror mounted on the bob. The theoretical analyses of these instruments does not rigorously account for the viscous effects in the bulk phases, but instead assumes that this viscous traction does not affect the interface. In one theoretical estimation of the viscous interaction effects in torsional surface viscometers, it has been found that this assumption of perfect slippage of the surface film can cause serious error for low surface viscosities of less than 1 surface poise. Hence, these methods are valid only for relatively large apparent interfacial viscosities such that the effects of viscous forces in the adjacent bulk phases can be neglected.

The most widely used method for the measurement of surface shear viscosity at gas-liquid interfaces is the deep channel surface viscometer. In this design, fluid motion is generated in a circular canal with fixed walls and ceiling by rotating the floor of the canal located at a known depth below the surface. A circular design was used to eliminate the surface pressure gradients associated with earlier linear canal viscometers. The velocity distribution of particles floating at the gas-liquid interface is measured and analyzed to calculate the surface shear viscosity.

Newer techniques have recently appeared. In one design for a surface shear viscometer of high sensitivity, an interfacial film is driven by contact with a rotating ring inserted in a narrow gap in the wall of a cylindrical vessel. The practical limits of the instrument were somewhat narrow.

In another design a longitudinal wave apparatus was developed which allows the measurement of a combination of surface rheological properties by analysis of surface waves at liquid-gas interfaces. This instrument does not measure the surface shear viscosity or dilational viscosity, but a combination of these properties. For the determination of surface dilational viscosity, this instrument must be used in conjunction with a surface shear viscosity apparatus such as the deep channel surface viscometer. The application of this apparatus has been extended to include measurements at liquid-liquid interfaces.

In a new procedure for estimating the total interfacial viscosity (shear plus dilational) of oil/water/surfactant sytems, the method involves the measurement of droplet-droplet coalescence rates in an inclined, spinning drop instrument commonly used for interfacial tension measurements. This procedure is much easier than those previously described, but offers only order of magnitude determinations.

To date, few designs exist which allow measurement of interfacial shear viscosities at liquid-liquid interfaces. Investigators have extended the analysis and applicability of the deep channel geometry to liquid-liquid systems and have provided the theoretical analysis for use of the thin disk and biconical bob geometries at liquid-liquid interfaces. The deep channel procedure requires a complicated apparatus which is difficult to clean and tedious to use. Clean surfaces are essential for the measurement of surface properties, since minute quantities of contaminates can seriously affect results. Furthermore, the experimental difficulties are magnified for liquid-liquid systems when the top phase is opaque. The thin disk and biconical bob are more simple experimentally but, as stated earlier, are limited in sensitivity.

A recent procedure, the "cup-of-tea" method was developed for the measurement of liquid-gas surface shear viscosity. This method involves the observation of decaying surface motions of a cup of liquid following sudden cessation of rigid body rotation. Small particles are floated on the surface to serve as tracers. The rate of decay of these surface motions is strongly affected by the shear viscosity of the liquid-gas interface. The surface shear viscosity is determined from measurements of original cup angular speed, cup geometry, surface particle angular displacement, and bulk fluid properties. Angular displacement measurments for water/air and oil/air systems which have negligibly small surface shear viscosities show good agreement with those predicted theoretically.

The new, novel invention described in this patent application is a further development in the design of surface viscometers directed to the liquid/liquid case. This non-obvious, new device and corresponding, unique method of measurement has an experimental design much more simple, more easily cleaned and used, and less expensive to construct than prior designs. In addition, this novel, new method appears to be sufficiently sensitive and adaptive to have a wide range of applications.

SUMMARY OF THE INVENTION

Two fluids are contained in a slowly turning cylindrical cell. The motion of the cell is abruptly halted and the deformation of the interface is measured with the use of tracer particles at the interface. The interfacial shear viscosity between the two fluids is determined by observation of the deformation of the fluid-fluid interface after the slowly rotating cylinder containing the two fluids is brought to an abrupt halt. The geometry of the rotating cylinder is illustrated in Graph 1. The cell radius is $R^*$ and its total height is $H_t^*$. The interface between the fluids is located at height $H_i^*$. Initially, the fluids are assumed to rotate as a rigid body at constant speed $W_o^*$. The equations of motion for the bulk phases and the interface are solved to determine the total angle of displacement on the interface as a function of radius and interfacial shear viscosity. Assuming Newtonian flow behavior and laminar flow only, the equation of motion for the bulk phases is derived from:

$$\frac{\partial^2 u}{\partial r^2} + \frac{1}{r}\frac{\partial u}{\partial r} - \frac{u}{r^2} + \frac{\partial^2 u}{\partial z^2} = \frac{\partial u}{\partial t}$$

where u (t,r,z) is dimensionless velocity in the angular direction defined as $$u = \frac{u^*}{R^* \omega^*_o}$$

Where
- $\omega_o^*$ = initial angular velocity (rad/sec)
- $u^*$ = velocity in angular direction
- t = is dimensionless time (t = t* V/R*)
- t* = time from halt of cell
- v = kinematic viscosity of the liquid
- z = dimensionless height (z = z*/R*)
- z* = height
- r = dimensionless radial distance (r = r*/R*)
- r* = radial distance.

The solution for the bottom phase must satisfy the following boundary conditions:

$u(0,t,z)=0$
$u(1,t,z)=0$
$u(r,t,0)=0$

For the top phase the boundary conditions are:

$u(0,t,z)=0$
$u(1,t,z)=0$
$u(r,t,H_t)=0$ where $H_t$ = value of z at $z^* = H_t^*$.

Assuming rigid body rotation of the fluid before the halt, the initial condition in the bulk phases and at the interface is $u(r,0,z)=r$ The discontinuity of dimensionless time, t, across the interface prevents application of the straightforward method of solution employed by the "cup of tea" method. The model presented and disclosed in this new, novel invention forces homogeneous boundary conditions at the interface by the definition of the variable w(r,t).

Let w(r,t) be the velocity of the interface, let S (r,t,z) be a variable, and let $u = s_{(r,t,z)} + \zeta_{(z)} w_{(r,t)}$ Where (r,t,z), (z), and (r,t) are subscripts, $\zeta_{(0)} = 0; \; \zeta_{(H_i)} = 1$ $\bar{u} = \bar{s}_{(r,t,z)} + \bar{\zeta}_{(z)} w_{(r,t)}^2$ Where $\bar{\zeta}_{(H_i)} = 1; \; \bar{\zeta}_{(H_t)} = 0$ $H_i$ = value of z at $z^* = H_i^*$ The boundary conditions for the variable s are $s_{(r,t,o)} = 0$ $s_{(r,t,H_i)} = 0$ Similarly $\bar{s}_{(r,t,H_i)} = 0$ $\bar{s}_{(r,t,H_t)} = 0$ The resulting system of equations is non-homogeneous with homogeneous boundary conditions. The system is solved by expansion of the eigenvalues of the corresponding homogeneous system of partial differential equations. A parametric study was conducted with the model of this disclosure and is presented in Graph 2. For all theoretical predictions and experiments, the height of the interface was chosen to be half of the cell height.

The most important correlation predicted by the model of this disclosure is between the interfacial shear viscosity (IFSV) and the traversed angel. This correlation, which is shown in Graph 2, will indicate whether traversed angles are sufficiently affected by the interfacial shear viscosity to allow the method to be effective over an appreciable range of IFSV's. Graph 2 shows model predictions for a cell which is 6 cm in diameter. The dimensionless cell height, $H_t$, is 2.0 and the interface height, $H_i$, is 1.0. The phases are distilled water and pure toluene. It can be seen that for IFSV's ranging from 0.01 mNs/m to 3.0 mNs/m, the measured angle is sensitive to the interfacial shear viscosity. Hence, theoretically, the range of applicability of the new, novel method of this disclosure is good for systems of this type.

For a given cell radius, the traversed angle increases with cell height. This is due to the interface being further away from the drag of the cell top and bottom. There is a maximum height, however, beyond which there is no improvement in traversed angle. The radius of the cell wall strongly affects the measured angle. This is because of the reduction of the retarding action of the cell wall. Greatest angles would be obtained for cell radii approaching infinity. This illustrates that it is possible to increase the sensitivity of the method indefinitely by increasing the cell radius and height.

For the relationship between cell volume and traversed angle, for constant height, $H_t$, the volume necessary to ensure traversion of a given angle increases with that angle. It is clear that, in reality, a reasonable balance must be obtained between practical experimental considerations such as sample size and ease of measurement, and measurement sensitivity. For a given cell volume, traversed angle increases with decreasing height, $H_t$, at high values of $H_t$. There is an optimum height, however, below which the angle decreases with decreasing height. This optimum height is determined by an optimum ratio of total cell height to cell radius of approximately 2.0. This represents the ideal cell geometry.

The information provided by the parametric study indicates that it is possible to increase the sensitivity of the technique indefinitely, but that the price for increased sensitivity is a larger cell volume, which means an increase in the required sample size and perhaps technical difficulties during measurement. It should also be noted that an increase in the cell volume may cause greater velocities in the cell which can result in the occurrence of secondary flows in the cell. This can significantly distort measurements. However, those systems where sensitivity is most important (liquids with high bulk viscosities) are most likely to maintain laminar flow. For any given cell volume, the optimum ratio of total cell height to cell radius is approximately 2.0.

The design of the apparatus allows maximum sensitivity of the measured parameter, the total traversed angle, to the interfacial shear viscosity, while maintaining dimensions which are reasonable with respect to experimental procedures and sample size requirements.

It is an object of the present invention to provide novel, new means and a method of measuring fluid-fluid interfacial rheology simply and conveniently.

Another object of this invention is to provide a novel, new means and method of measuring liquid-liquid interfacial rheology and specifically interfacial shear viscosity. Current technology provides no adequate means for accurately accomplishing this.

A further object of this invention is to provide a novel, new means and method of measuring fluid-fluid interfacial rheology in which the apparatus is both simple in design and simple in use and thus conducive to routine measurements as well as easy to clean. Clean surfaces are essential for accurate measurement.

Yet another object of this invention is to provide a novel, new means and method of measuring liquid-liquid interfacial shear viscosities with sufficient sensitivity and accuracy to allow measurements ranging from 0.001 to 5.0 surface poise depending on cell geometry and liquid viscosity.

A still further object of this invention is to provide a novel, new means and method of measuring fluid-fluid rheological properties by observation from below of the interfacial deformation between two fluids. Current technology observes the fluids from the top so that if the upper fluid is not transparent measurement is not possible.

EXPERIMENT I

Experimental tests were performed to determine the compliance of the theoretical predictions discussed above with experimental data. The cylindrical cell chosen had a transparent bottom to allow video recording of tracer particle movement through the bottm phase, and the cell was connected at its top to a motor/gear-reducer. A stabilizing bearing and rubber shock absorber were used between the motor and cell to prevent the transfer of vibrations from the motor to the cell.

An experimental parametric study was conducted to establish the effect of parameters such as cell dimensions and liquid phase viscosities on the precision and accuracy of the method. Five different cells were used throughout the study as shown in Table 1.

TABLE 1

| Dimensions of Viscometer Cells | | |
|---|---|---|
| Cell No. | Diameter (cm) | Cell Height (cm) |
| 1 (Standard Cell) | 6.0 | 6.0 |
| 2 | 6.0 | 9.0 |
| 3 | 4.5 | 4.5 |
| 4 | 4.5 | 6.0 |
| 5 | 10.0 | 10.0 |

The top phase fluids used for the parametric study were toluene, decane and hexadecane. Distilled water was used as the bottom phase. The tests were done at room temperature. Deformation of the interface was established by measurement of the movement of cryolite tracer particles. All three fluids were tested in cells 1 and 3, and the decane/distilled water combination was tested in cells 2, 4 and 5. The initial rotational speed in the experiments was 0.12 rad/sec.

The parametric study investigated the following points:

(1) Effect of cell size on the accuracy and precision of the method;

(2) Effect of cell geometry (Height/Wall radius) on the accuracy and precision of the method; and (3) Effect of bulk phase viscosity on the accuracy and the precision of the method.

Table 2 shows the results of the parametric study. The liquids studied in this parametric study are pure hydrocarbons and distilled water, and the interfacial shear viscosity in these systems is expected to be negligible. Therefore, the deviation of the mean interfacial viscosity from zero is a measure of the accuracy of the method. The standard deviation is an indication of the precision of the method.

Table 2-A shows the effect of top phase viscosity on the mean measured interfacial shear viscosity and on the standard deviation in the standard cell (cell 1). It can be seen that the mean is within 0.001 of zero, which is the true IFSV (interfacial shear viscosity) for these systems. Therefore the accuracy is good. The standard deviation is found to increase with the viscosity. This was expected, since the sensitivity of the detected parameter (the traversed angle) to the measured parameter (IFSV) is reduced due to the fact that the effect of bulk viscosity on traversed angles is increased. Also, for the system with the more viscous bulk phase, the absolute value of the detected parameter, the angle, is decreased, which means an increase in the possibility of experimental error.

The effect of bulk phase viscosities in the smaller cell No. 3 is shown in Table 2-B. It is shown that, for the viscous hexadecane, the mean diverges from zero by the amount of 0.0025 sp, an inaccuracy which is significantly greater than those observed for the other liquids. The precision of the measurement also appears to be affected by the high viscosity of the hexadecane, since the observed standard deviation of 0.0051 exceeds the other observed standard deviation significantly.

Finally, the effect of cell dimensions for measurements on the decane/water system is listed in Table 2-C. For cells 1 through 4, no clear trend was found relating cell geometry or size to precision or accuracy. In cell 5, the experiment fails at the rotational speed of 0.12 rad/sec. Movement of tracer particles in the radial direction suggests the occurence of secondary currents, indicating that the assumption of laminar flow is invalid. When the rotational speed is reduced to 0.04 rad/sec., movement of tracer particles in the radial direction ceases. However, inspection of the data indicates that the experimental angles exceed theoretical predictions. This can be explained by noting that secondary currents, even when their presence can not be established visually, may increase traversed angles. The assumption of laminar flow in cell 5 with decane/water is apparently invalid.

The parametric study indicates that, for the cell sizes and the cell geometries studied, the experimental accuracy and precision for the method is apparently not affected by cell size and cell geometry with the exceptions of the system comprising the smallest cell (cell No. 3) containing the most viscous liquid (hexadecane) and the largest cell (cell No. 5). This indicates the existence of limitations in the applicability of the method both due to cell sizes which are too small (for viscous liquids) and cell sizes which are too great.

Room temperatures are important to determine as they may effect the rheological properties of fluids. Therefore, ambient temperature measurement means may be provided within the novel, new device of this invention.

TABLE 2

Experimental Parametric Study 2-a Viscosity Effect in Standard Cell

| Bulk Phase Fluid | Mean (sp) | Standard Deviation (sp) |
| --- | --- | --- |
| Toluene | 0.0007 | ±0.0006 |
| Decane | 0.0009 | ±0.0010 |
| Hexadecane | −0.0001 | ±0.0030 |

2-b Viscosity Effect in Cell No. 3

| Bulk Phase Fluid | Mean (sp) | Standard Deviation (sp) |
| --- | --- | --- |
| Toluene | 0.0003 | ±0.0010 |
| Decane | −0.0006 | ±0.0007 |
| Hexadecane | −0.0025 | ±0.0051 |

2-c Effect of Cell Size (Decane/Water)

| Cell Number | Mean (sp) | Standard Deviation (sp) |
| --- | --- | --- |
| 1 | 0.0009 | ±0.0006 |
| 2 | 0.0001 | ±0.0007 |
| 3 | −0.0006 | ±0.0007 |
| 4 | 0.0013 | ±0.0012 |
| 5 | 0.0084 | ±0.0018 |

IN THE DRAWINGS

The novel features of the present invention are set forth with particularity in the appended claims. The invention, together with further objects and advantages thereof, may be best understood by way of the following description of exemplary apparatus employing the principles of the invention as illustrated in the accompanying drawings in which:

FIG. 1 depicts the cylindrical sample cell of a preferred embodiment of a new and improved apparatus for practicing the invention and incorporating its principles; and FIG. 2 shows a schematic representation of the new, novel apparatus of this invention as the device will appear in its operating position measuring interfacial rheological properties.

DETAILED DESCRIPTION OF PREFERRED EMBODIMENT

Figure 1:
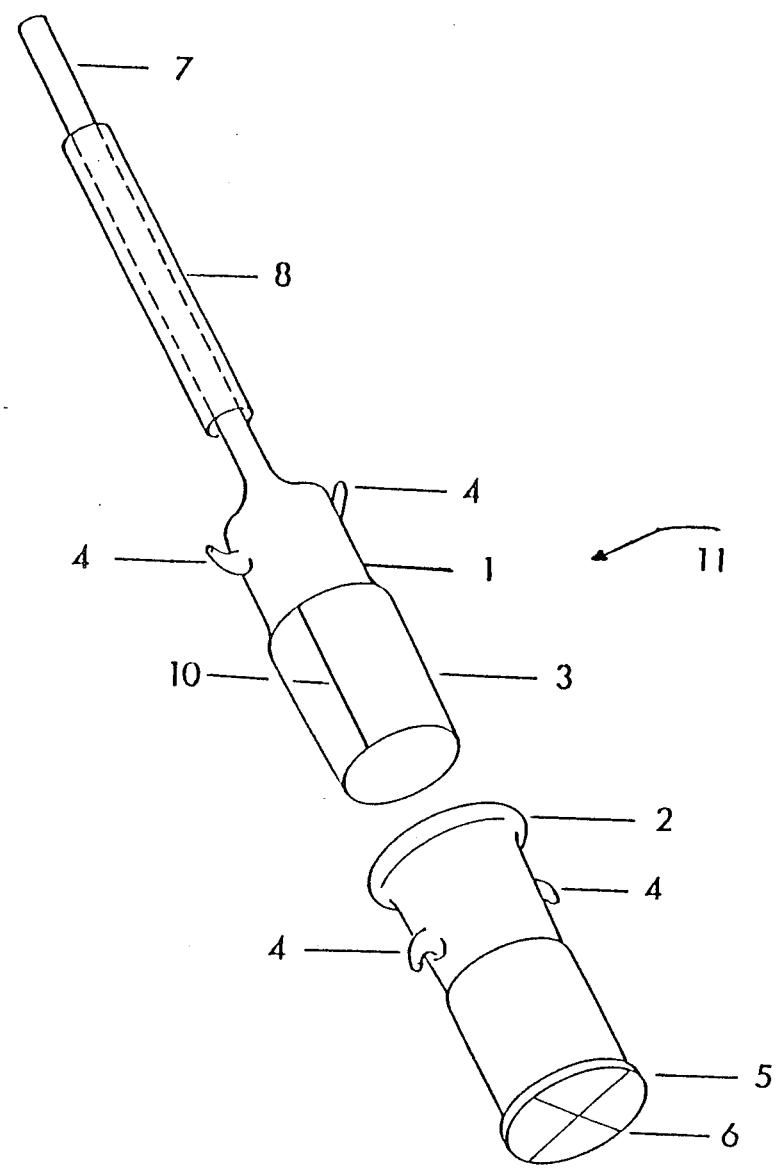

Turning now to the drawings, and first to FIG. 1, one embodiment of the cylindrical cell for use in the new novel apparatus of this disclosure for measuring fluid-fluid interfacial rheological properties incorporating the principles of the present invention is illustrated generally at 11.

The cylindrical cell 11 is shown broken apart to reveal its parts. The cell body 2 and the cell top 1 are composed of glass in this embodiment but another alternative embodiment could be of any transparent material to allow light to enter to enable visibility. The cell body 2 joins the cell top 11 with seal means 3. The seal means 3 may incorporate a glass fitting allowing for an air tight seal between the cell body 2 and the cell top 1 when the cylindrical cell 11 is composed of glass. An air vent groove 10 is placed upon the seal means 3 to allow overflow fluid to escape when closing the celltop 1. Hooks 4 are provided to secure the cell top 1 to the cell body 2 after closing with springs or other flexible closure means.

The cell body 2 is provided with a flat transparent bottom 5. The bottom 5 is inscribed with increment measurement means 6 which can be as simple as cross hairs etched upon the surface of the bottom 5.

A drive shaft 7 extends from the top of the cell top 1 through a support bearing 8. When the cell top 1 is composed of glass the drive shaft 7 may be also of glass and be attached to the cell top by melting them together. The support bearing 8 in this case may be a ground glass fitting within a glass collar.

Figure 2:
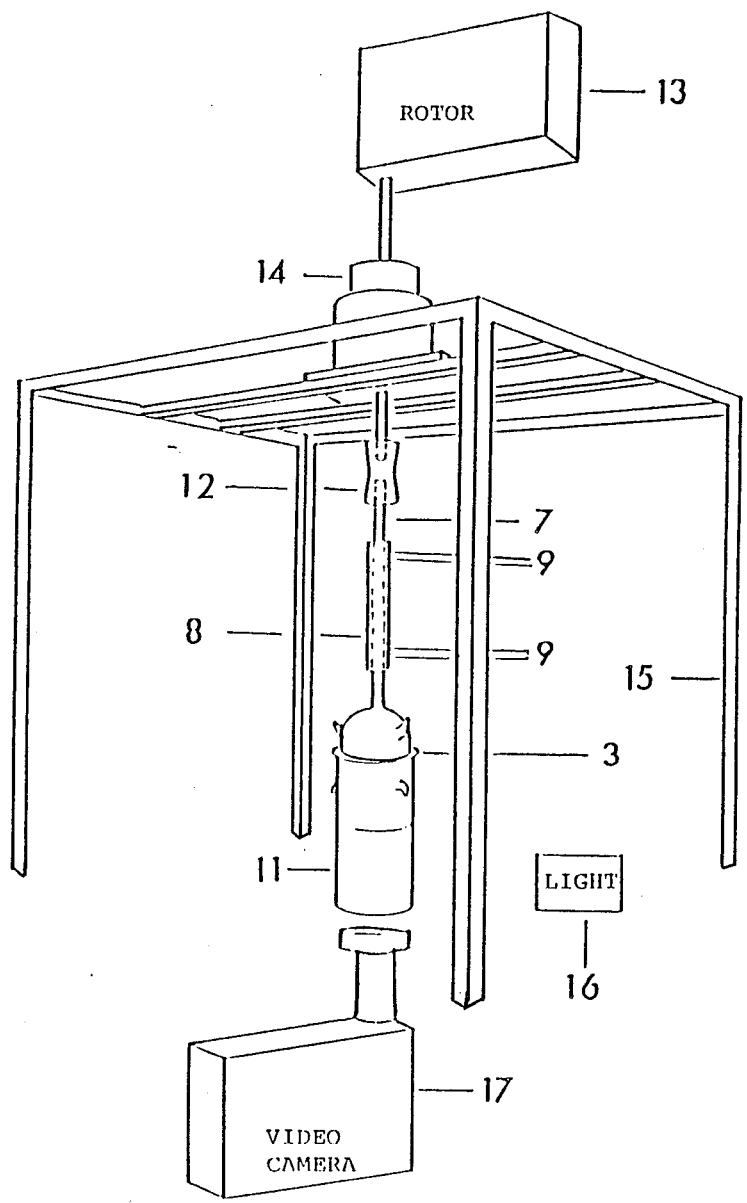

In FIG. 2 is illustrated the entire novel, new apparatus for measuring fluid-fluid interfacial rheological properties shown as it generally appears during the course of a typical measuring operative.

The cylindrical cell 11 is in position for testing frame means 15 supports the apparatus. Seal means 3 closes the cylindrical cell 11 airtight and the drive shaft 7 is positioned within the support bearing 8. The support bearing 8 is independently supported by braces 9 so that vibrations are dampened. A flexible collar 12 is provided along the drive shaft to further dampen vibrations.

A circular rotor 13 is suspended above the cylindrical cell 11 and supported by frame means 15. The circular rotor 13 slowly rotates the drive shaft 7. The drive shaft 7 passed through a gear reduction means 14 to enable the rotation of the cylindrical cell 11 to be abruptly halted. The drive shaft 7 then passes through the flexible collar 12, through the support bearing 8 and attaches to the top of the cylindrical cell 11. The circular rotor 13 is positioned so that the axis of the circular rotor 13, the drive shaft 7 and the cylindrical cell 11 are all concentric. When the circular rotor 13 slowly turns the drive shaft 7, the cylindrical cell 11 will also slowly turn. An observing means 17 such as a video camera is provided for observing through the bottom of the cylindrical cell 11. An alternative light source 16 is provided to further enable the visibility through the cylindrical cell 11. Ambient temperature measurement means may also be provided within the apparatus to record ambient temperature.

In order to measure fluid-fluid interfacial rheological properties the cylindrical cell top 1 is removed from the cell body 2. A first fluid to be tested is placed in the cell body 2 until the cell body 2 is one half full. This first fluid must be transparent in order to allow visibility. Minute tracer particles are placed carefully on top of th first fluid. Cryolite particles and wood particles have been used successfully. A second fluid to be tested is now carefully placed in the cell body 2 on top of the tracer particles. This second fluid must be lighter than the first fluid in order to maintain separation. The cell top 1 may now be inserted into the cell body 2 and seal means seamed. The air vent groove 10 enables any excess second fluid to bleed off. The observation means 17 is placed under the bottom 5 of the cylindrical cell 11 so that the interface containing the tracer particles between the first and second fluids may be observed. The increment measurement means 6 may also be observed at the same time in order to detect the deformation of the tracer particles at the interface of the first and second fluids. The alternative light source 16 provides additional light to enable better visibility of the interface.

The circular rotor 13 slowly rotates the drive shaft 7 and in turn the cylindrical cell 11. This slow rotation causes both fluids within the cell to move and at a set time interval the rotation is abruptly halted by means of the gear reduction 14. Such an immediate halt causes deformation of the interface between the fluids affecting the tracer particles. It is necessary that the halt be immediate for best results. Observation means 17 loking up through the bottom 5 of the cylindrical cell 11 observes the resulting deformation and with the aid of increment measurement means 6 inscribed on the bottom 5 of the cylindrical cell the deformation may be measured. With the application of the theory and method of this invention various fluid-fluid rheological properties may be found including interfacial shear viscosity.

While only a particular embodiment of the present invention and one mode of practicing the invention have been shown and described, it is apparent that changes and modifications may be made without departing from this invention in its broader aspects, therefore the aim in the appended claims is to cover all such changes and modifications as fall within the true spirit and scope of this invention.

What is claimed is:

1. Apparatus for measuring fluid-fluid interfacial rheology comprising:
   A. a cylindrical cell capable of containing fluids and having a closed transparent bottom and a top capable of being opened and closed with seal means; and
   B. means attaching a drive shaft to said top; and
   C. a circular rotor suspended above said cylindrical cell such that the lower surface of said rotor contacts said drive shaft through connecting means and said rotor and said drive shaft are positioned such that the axis of said rotor and said drive shaft drive are concentric with the axis of said cylindrical cell, and freely rotatable about said axis of said cylindrical cell; and
   D. means for observing through said bottom of said cylindrical cell; and
   E. frame support means supporting said cylindrical cell and suspending said rotor.

2. The apparatus of claim 1 wherein said drive shaft contains a flexible portion.

3. The apparatus of claim 2 wherein said flexible portion of said drive shaft is a collar.

4. The apparatus of claim 1 wherein said rotor has variable speed control means.

5. The apparatus of claim 1 wherein said cylindrical cell dimensions are a ratio of total cell height to cell radius of 2.

6. The apparatus of claim 1 wherein said observing means further includes a recording means.

7. The apparatus of claim 1 further including ambient temperature measurement means.

8. The apparatus of claim 1 wherein said bottom of said cylindrical cell is flat.

9. The apparatus of claim 1 wherein said bottom of said cylindrical cell is composed of a transparent lens.

10. The apparatus of claim 9 wherein said bottom of said cylindrical cell is inscribed with increment measurement means visible to said observing means.

11. The apparatus of claim 1 further including vent means through said top of said cylindrical cell.

12. The apparatus of claim 1 further including a vibration dampening means positioned in the axis line between said circular rotor and said cylindrical cell.

13. The apparatus of claim 12 wherein said vibration dampening means is a collar.

14. The apparatus of claim 1 further including bearing means in the axis line between said circular rotor and said cylindrical cell.

15. The apparatus of claim 14 wherein said bearing means is comprised of a ground glass fitting.

16. The apparatus of claim 14 wherein said bearing means is independently supported and not fixed to said frame support means.

17. A method for measuring fluid-fluid interfacial rheology comprising the steps of:
   A. filling a cylindrical cell with the first fluid to be measured,
   B. placing tracer particles on the top of said fluid to be measured,
   C. topping off said cylindrical cell with the second fluid to be measured,
   D. closing off said cylindrical cell by seal means so that the cell is air tight,
   E. rotating said cylindrical cell slowly,
   F. halting said rotating of said cylindrical cell abruptly, so that deformation of the interface between first and second said fluids affects said tracer particles located at the interface of said first and second fluids, and
   G. detecting said deformation of said tracer particles by observation means through a transparent bottom formed on said cylindrical cell.

18. The method of claim 17 wherein said cylindrical cell is rotated slowly by:
   suspending a rotor above said cylindrical cell.

19. The method of claim 18 wherein said cylindrical cell is halted abruptly by:
   reducing gears of said rotor so that the interface between said first and second fluids is deformed instantaneously.

20. The method of claim 19 wherein the detection of deformation of said tracer particles is improved by:
   dampening out vibrations caused by said rotor by inserting a flexible section between said rotor drive shaft and said cylindrical cell and by mounting, independently of said rotor and said cylindrical cell, a bearing between said rotor and said cylindrical cell to support said rotor drive shaft.

* * * * *